(12) United States Patent
Rosenquist

(10) Patent No.: US 8,790,330 B2
(45) Date of Patent: Jul. 29, 2014

(54) CONNECTION ARRANGEMENT AND METHOD FOR CONNECTING A MEDICAL DEVICE TO THE IMPROVED CONNECTION ARRANGEMENT

(75) Inventor: Tobias Rosenquist, Kallered (SE)

(73) Assignee: Carmel Pharma AB, Gothenburg (SE)

( * ) Notice: Subject to any disclaimer, the term of this patent is extended or adjusted under 35 U.S.C. 154(b) by 990 days.

(21) Appl. No.: 12/335,207

(22) Filed: Dec. 15, 2008

(65) Prior Publication Data
US 2010/0152669 A1    Jun. 17, 2010

(51) Int. Cl.
- *A61M 25/16* (2006.01)
- *A61M 5/32* (2006.01)
- *A61M 5/00* (2006.01)

(52) U.S. Cl.
USPC ............ 604/533; 604/192; 604/241; 604/257

(58) Field of Classification Search
USPC ......... 604/533, 535, 192, 241, 257, 403, 411, 604/414
See application file for complete search history.

(56) References Cited

U.S. PATENT DOCUMENTS

| | | |
|---|---|---|
| 1,844,342 A | 2/1932 | Berman |
| 2,010,417 A | 8/1935 | Schwab |
| 2,697,438 A | 12/1954 | Hickey |
| 2,717,599 A | 9/1955 | Huber |
| 3,064,651 A | 11/1962 | Henderson |
| 3,071,135 A | 1/1963 | Baldwin et al. |
| 3,308,822 A | 3/1967 | DeLuca |
| 3,316,908 A | 5/1967 | Burke |
| 3,340,671 A | 9/1967 | Loo |
| 3,390,677 A | 7/1968 | Razimbaud |
| 3,448,740 A | 6/1969 | Figge |
| 3,542,240 A | 11/1970 | Solowey |
| 3,783,895 A | 1/1974 | Weichselbaum |
| 3,788,320 A | 1/1974 | Dye |

(Continued)

FOREIGN PATENT DOCUMENTS

| | | |
|---|---|---|
| AU | 200112863 | 5/2003 |
| DE | 2005519 | 10/1979 |

(Continued)

OTHER PUBLICATIONS

International Search Report PCT/EP2008/067535 mailed Oct. 21, 2009 (3 pages).

(Continued)

*Primary Examiner* — Kami A Bosworth
*Assistant Examiner* — Imani Hayman
(74) *Attorney, Agent, or Firm* — Servilla Whitney LLC

(57) ABSTRACT

The present invention relates to a connection arrangement and a method of assembly, for providing a substantially tamper resistant connection with at least a first medical device. The connection arrangement having a center axis, the connection arrangement comprises; a first connection member for connection to the first medical device by means of a rotational motion in a first direction, and a body. Additionally the first connection member and the body are connected directly or indirectly together via at least one designated ruptureable retaining member, the designated ruptureable retaining member is arranged to rupture at a predetermined breaking force, wherein the first connection member, and thereby the first medical device after assembly, can be displaced with respect to the body after rupture. The present invention provides for a substantially tamper safe connection arrangement which disables accidents such as wrongly disengage a connected medical device. A safer handling is provided for the involved user(s).

28 Claims, 9 Drawing Sheets

(56) References Cited

U.S. PATENT DOCUMENTS

| | | |
|---|---|---|
| 3,822,700 A | 7/1974 | Pennington |
| 3,938,520 A | 2/1976 | Scislowicz et al. |
| 3,976,073 A | 8/1976 | Quick et al. |
| 4,096,860 A | 6/1978 | McLaughlin |
| 4,296,786 A | 10/1981 | Brignola |
| D270,568 S | 9/1983 | Armstrong |
| 4,490,139 A | 12/1984 | Huizenga et al. |
| 4,516,967 A | 5/1985 | Kopfer |
| 4,564,054 A | 1/1986 | Gustavsson |
| 4,573,967 A | 3/1986 | Hargrove et al. |
| 4,576,211 A | 3/1986 | Valentini et al. |
| 4,581,016 A | 4/1986 | Gettig |
| 4,582,223 A | 4/1986 | Kobe |
| 4,588,403 A | 5/1986 | Weiss et al. |
| 4,600,040 A | 7/1986 | Naslund |
| 4,623,343 A | 11/1986 | Thompson |
| 4,629,455 A | 12/1986 | Kanno |
| 4,632,673 A | 12/1986 | Tiitola et al. |
| 4,636,204 A | 1/1987 | Christopherson et al. |
| 4,673,400 A | 6/1987 | Martin |
| 4,673,404 A | 6/1987 | Gustavsson |
| 4,737,150 A | 4/1988 | Baeumle et al. |
| 4,752,287 A | 6/1988 | Kurtz et al. |
| 4,759,756 A | 7/1988 | Forman et al. |
| 4,768,568 A | 9/1988 | Fournier et al. |
| 4,792,329 A | 12/1988 | Schreuder |
| 4,804,015 A | 2/1989 | Albinsson |
| 4,822,340 A | 4/1989 | Kamstra |
| 4,826,492 A | 5/1989 | Magasi |
| 4,834,717 A | 5/1989 | Haber et al. |
| 4,842,585 A | 6/1989 | Witt |
| 4,850,978 A | 7/1989 | Dudar et al. |
| 4,864,717 A | 9/1989 | Baus, Jr. |
| 4,872,494 A | 10/1989 | Coccia |
| 4,878,897 A | 11/1989 | Katzin |
| 4,889,529 A | 12/1989 | Haindl |
| 4,898,209 A | 2/1990 | Zbed |
| 4,909,290 A | 3/1990 | Coccia |
| 4,932,937 A | 6/1990 | Gustavsson et al. |
| 4,944,736 A | 7/1990 | Holtz |
| 4,964,855 A | 10/1990 | Todd et al. |
| 4,982,769 A | 1/1991 | Fournier et al. |
| 4,994,048 A | 2/1991 | Metzger |
| 4,997,083 A | 3/1991 | Loretti et al. |
| 5,017,186 A | 5/1991 | Arnold |
| 5,041,105 A | 8/1991 | D'Alo et al. |
| 5,061,264 A | 10/1991 | Scarrow |
| 5,071,413 A | 12/1991 | Utterberg |
| 5,122,116 A | 6/1992 | Kriesel et al. |
| 5,122,123 A | 6/1992 | Vaillancourt |
| 5,137,524 A | 8/1992 | Lynn et al. |
| 5,158,554 A | 10/1992 | Jepson et al. |
| 5,176,673 A | 1/1993 | Marrucchi |
| 5,199,947 A | 4/1993 | Lopez et al. |
| 5,201,725 A | 4/1993 | Kling |
| 5,207,658 A | 5/1993 | Rosen et al. |
| 5,232,109 A | 8/1993 | Tirrell et al. |
| 5,254,097 A | 10/1993 | Schock et al. |
| 5,279,576 A | 1/1994 | Loo et al. |
| 5,279,583 A | 1/1994 | Shober, Jr. et al. |
| 5,279,605 A | 1/1994 | Karrasch et al. |
| 5,308,347 A | 5/1994 | Sunago et al. |
| 5,312,366 A | 5/1994 | Vaillancourt |
| 5,328,480 A | 7/1994 | Melker et al. |
| 5,334,163 A | 8/1994 | Sinnett |
| 5,356,406 A | 10/1994 | Schraga |
| 5,385,545 A | 1/1995 | Kriesel et al. |
| 5,385,547 A | 1/1995 | Wong et al. |
| 5,389,085 A | 2/1995 | D'Alessio et al. |
| 5,405,326 A | 4/1995 | Haber et al. |
| 5,445,630 A | 8/1995 | Richmond |
| 5,447,501 A | 9/1995 | Karlsson et al. |
| 5,456,675 A | 10/1995 | Wolbring et al. |
| 5,470,522 A | 11/1995 | Thome et al. |
| 5,478,328 A | 12/1995 | Silverman et al. |
| 5,478,337 A | 12/1995 | Okamoto et al. |
| 5,492,531 A | 2/1996 | Post et al. |
| 5,514,117 A | 5/1996 | Lynn |
| 5,515,871 A | 5/1996 | Bittner et al. |
| 5,536,259 A | 7/1996 | Utterberg |
| 5,575,780 A | 11/1996 | Saito |
| 5,593,028 A | 1/1997 | Haber et al. |
| 5,613,954 A | 3/1997 | Nelson et al. |
| 5,632,735 A | 5/1997 | Wyatt et al. |
| 5,647,845 A | 7/1997 | Haber et al. |
| 5,685,866 A | 11/1997 | Lopez |
| 5,752,942 A | 5/1998 | Doyle et al. |
| 5,766,147 A | 6/1998 | Sancoff et al. |
| 5,766,211 A | 6/1998 | Wood et al. |
| 5,782,872 A | 7/1998 | Muller |
| 5,795,336 A | 8/1998 | Romano et al. |
| 5,817,083 A | 10/1998 | Shemesh et al. |
| 5,820,609 A | 10/1998 | Saito |
| 5,827,262 A | 10/1998 | Neftel et al. |
| 5,837,262 A | 11/1998 | Golubev et al. |
| 5,875,931 A | 3/1999 | Py |
| 5,879,345 A | 3/1999 | Aneas |
| 5,897,526 A | 4/1999 | Vaillancourt |
| 5,934,510 A | 8/1999 | Anderson |
| 5,984,899 A | 11/1999 | D'Alessio et al. |
| 6,063,068 A | 5/2000 | Fowles et al. |
| D427,308 S | 6/2000 | Zinger |
| 6,070,623 A | 6/2000 | Aneas |
| 6,071,270 A | 6/2000 | Fowles et al. |
| 6,090,091 A | 7/2000 | Fowles et al. |
| 6,113,068 A | 9/2000 | Ryan |
| 6,113,583 A | 9/2000 | Fowles et al. |
| 6,142,446 A | 11/2000 | Leinsing |
| 6,146,362 A | 11/2000 | Turnbull et al. |
| 6,209,738 B1 | 4/2001 | Jansen et al. |
| 6,221,065 B1 | 4/2001 | Davis |
| 6,245,056 B1 | 6/2001 | Walker et al. |
| D445,501 S | 7/2001 | Niedospial, Jr. |
| 6,253,804 B1 | 7/2001 | Safabash |
| 6,258,078 B1 | 7/2001 | Thilly |
| 6,387,074 B1 | 5/2002 | Horppu et al. |
| 6,453,956 B2 | 9/2002 | Safabash |
| 6,471,674 B1 | 10/2002 | Emig et al. |
| 6,517,523 B1 | 2/2003 | Kaneko et al. |
| 6,537,263 B1 | 3/2003 | Aneas |
| 6,571,837 B2 | 6/2003 | Jansen et al. |
| 6,591,876 B2 | 7/2003 | Safabash |
| 6,644,367 B1 | 11/2003 | Savage et al. |
| 6,685,692 B2 | 2/2004 | Fathallah |
| 6,715,520 B2 | 4/2004 | Andreasson et al. |
| 6,761,286 B2 | 7/2004 | Py et al. |
| D495,416 S | 8/2004 | Dimeo et al. |
| 6,786,244 B1 | 9/2004 | Jones |
| D506,256 S | 6/2005 | Miyoshi et al. |
| 6,960,194 B2 | 11/2005 | Hommann et al. |
| 7,000,806 B2 | 2/2006 | Py et al. |
| 7,080,672 B2 | 7/2006 | Fournier et al. |
| 7,297,140 B2 | 11/2007 | Orlu et al. |
| D570,477 S | 6/2008 | Gallogly et al. |
| D572,820 S | 7/2008 | Gallogly et al. |
| D577,438 S | 9/2008 | Gallogly et al. |
| D577,822 S | 9/2008 | Gallogly et al. |
| D582,033 S | 12/2008 | Baxter et al. |
| D605,755 S | 12/2009 | Baxter et al. |
| 7,703,486 B2 | 4/2010 | Costanzo |
| D616,984 S | 6/2010 | Gilboa |
| 7,744,581 B2 | 6/2010 | Wallen et al. |
| 2001/0021825 A1 | 9/2001 | Becker et al. |
| 2001/0025671 A1 | 10/2001 | Safabash |
| 2002/0002352 A1 | 1/2002 | Becker et al. |
| 2002/0082586 A1 | 6/2002 | Finley et al. |
| 2002/0127150 A1 | 9/2002 | Sasso |
| 2002/0177819 A1 | 11/2002 | Barker et al. |
| 2003/0010717 A1 | 1/2003 | Brugger et al. |
| 2003/0070726 A1 | 4/2003 | Andreasson et al. |
| 2003/0106610 A1 | 6/2003 | Roos et al. |
| 2003/0107628 A1 | 6/2003 | Fowles et al. |
| 2003/0199846 A1 | 10/2003 | Fowles et al. |
| 2003/0233083 A1 | 12/2003 | Houwaert et al. |

(56) References Cited

U.S. PATENT DOCUMENTS

| | | |
|---|---|---|
| 2004/0116858 A1 | 6/2004 | Heinz et al. |
| 2004/0199139 A1 | 10/2004 | Fowles et al. |
| 2004/0215147 A1 | 10/2004 | Wessman et al. |
| 2005/0215977 A1 | 9/2005 | Uschold |
| 2006/0025747 A1 | 2/2006 | Sullivan et al. |
| 2006/0106360 A1 | 5/2006 | Wong |
| 2006/0111667 A1 | 5/2006 | Matsurra et al. |
| 2006/0157984 A1 | 7/2006 | Rome et al. |
| 2006/0186045 A1 | 8/2006 | Jensen et al. |
| 2007/0021725 A1 | 1/2007 | Villette |
| 2007/0060841 A1 | 3/2007 | Henshaw |
| 2007/0088313 A1 | 4/2007 | Zinger et al. |
| 2007/0106244 A1 | 5/2007 | Mosler et al. |
| 2007/0179441 A1 | 8/2007 | Chevallier |
| 2007/0270759 A1 | 11/2007 | Pessin |
| 2007/0270778 A9 | 11/2007 | Zinger et al. |
| 2008/0045919 A1 | 2/2008 | Jakob et al. |
| 2008/0103453 A1 | 5/2008 | Liversidge |
| 2008/0103485 A1 | 5/2008 | Kruger |
| 2008/0172039 A1 | 7/2008 | Raines |
| 2008/0223484 A1 | 9/2008 | Horppu |
| 2008/0287920 A1* | 11/2008 | Fangrow et al. ............. 604/535 |
| 2008/0312634 A1 | 12/2008 | Helmerson et al. |
| 2009/0254042 A1 | 10/2009 | Gratwohl et al. |
| 2010/0137827 A1 | 6/2010 | Warren et al. |
| 2010/0204671 A1 | 8/2010 | Kraushaar et al. |
| 2010/0243099 A1 | 9/2010 | Yodfat |

FOREIGN PATENT DOCUMENTS

| | | |
|---|---|---|
| EP | 0255025 | 2/1988 |
| EP | 0259582 | 3/1988 |
| EP | 0285424 | 10/1988 |
| EP | 0311787 | 4/1989 |
| EP | 0376629 | 7/1990 |
| EP | 0803267 | 10/1997 |
| EP | 0819442 | 1/1998 |
| EP | 0995453 | 4/2000 |
| EP | 1060730 | 12/2000 |
| EP | 1484073 | 12/2004 |
| EP | 1731128 | 12/2006 |
| FR | 2757405 | 6/1998 |
| FR | 2780878 | 1/2000 |
| GB | 1579065 | 11/1980 |
| JP | 49-12690 | 5/1972 |
| JP | 288664 | 7/1990 |
| JP | 3030963 | 8/1996 |
| JP | 2000167022 | 6/2000 |
| JP | 2001505092 | 4/2001 |
| JP | 2001293085 | 10/2001 |
| TW | 482670 | 4/2002 |
| WO | WO 84/04672 | 12/1984 |
| WO | WO 84/04673 | 12/1984 |
| WO | WO 90/03536 | 4/1990 |
| WO | WO 98/19724 | 5/1998 |
| WO | WO 99/27886 | 6/1999 |
| WO | WO 99/62578 | 12/1999 |
| WO | WO 00/05292 | 2/2000 |
| WO | WO 00/35517 | 6/2000 |
| WO | WO 01/80928 | 11/2001 |
| WO | WO 02/02048 | 1/2002 |
| WO | WO 02/11794 | 2/2002 |
| WO | WO 02/064077 | 8/2002 |
| WO | WO 02/076540 | 10/2002 |
| WO | WO 2005/074860 | 8/2005 |
| WO | WO 2006/082350 | 8/2006 |
| WO | WO-2006/083333 | 8/2006 |
| WO | WO2006/083333 | 8/2006 |
| WO | WO2008/028305 | 3/2008 |
| WO | WO2008115102 | 9/2008 |
| WO | WO-2008/144447 | 11/2008 |
| WO | WO 2006/138184 | 12/2009 |

OTHER PUBLICATIONS

Taiwan Search Report for Taiwan Patent Application 092106323 dated Mar. 21, 2003 (4 pages).
Japan Application No. 2003-583539, Official Action dated May 1, 2009 (3 pages).
Japan Application No. 2003-577789, Official Action dated Feb. 24, 2009 (4 pages).
International Search Report, PCT/EP2008/067522 dated Aug. 12, 2009 (2 pages).
Extended EP Search Report in EP13180902.2, dated Oct. 15, 2013, 6 pgs.
Official Notice of Rejection, mailed on Mar. 26, 2013, for Japanese Patent Application No. 2011-514428, which corresponds to this patent application.

* cited by examiner

CONNECTION ARRANGEMENT AND METHOD FOR CONNECTING A MEDICAL DEVICE TO THE IMPROVED CONNECTION ARRANGEMENT

TECHNICAL FIELD

The present invention relates to a connection arrangement for providing at least one medical device with a tamper resistant connection and a method for connecting the at least one medical device to the connection arrangement.

BACKGROUND OF THE INVENTION

During medical procedures, operations, administration of drugs or other activities involving medical instruments, it is important that the individual instruments are securely attached together. Instruments which are inadequately connected run the risk of being disconnected, which could potentially expose hazardous medicaments such as cytotoxins, neurotoxins or the like. Further persons dealing with piercing members, e.g. a nurse or a patient, run the risk of being accidentally exposed to the tip of a piercing member which potentially could rupture the skin of a user. The severity of such an incident can range from a low risk level to a substantially lethal risk level, for example when dealing with the HIV virus. However, not only accidents can cause such situations, doctors, nurses, caring personal and even patients can accidentally disconnect the wrong medical instrument. Such an error can potentially impart a high risk situation to the involved persons. There seem to be a need for tamper safe devices and tamper safe connections.

Medical adaptor devices are vital to connect and enable administration of e.g. drugs between vials and syringes or any other medical devices as the range of products, combinations and functions are vast. In the patent with the U.S. Pat. No. 4,629,455 a medical instrument arrangement is disclosed. The medical instrument arrangement incorporates a female connector member having a female taper portion and a male connector member having a male taper portion. The female connector member has threads for cooperative engagement with a rotary ring, adapted to rotate freely around the longitudinal axis of the male connector member. The rotary ring further comprises threads for cooperative engagement with the threads of the female connector member. The threads of the rotary ring exhibit a rotary thread ridge which is adapted to fracture a rib arranged on the threads of the female connector member. The fracture of the rib provides for an increased friction between the threads of the female connector member and the threads of the rotary ring, keeping the two connected parts firmly in place and hence substantially tamper safe. There are however drawbacks with this medical instrument arrangement which will be readily apparent.

US 2004/016858 A1 provides for another substantially tamper safe device in the form of a tamper safe closure for a syringe with a luer connection or a luer lock connection. A cap is connected to the syringe via a frangible web which after rupture permits removal of the cap from the syringe. The tamper safe closure does not however provide for any tamper safe means with respect to the device which is connected to the syringe.

SUMMARY OF THE INVENTION

It is an object of the present invention to at least partly solve some of the above mentioned drawbacks. More specifically they are at least partly solved by a connection arrangement providing at least a first medical device with a substantially tamper resistant connection. The connection arrangement may exhibit a centre axis. The connection arrangement comprises a first connection member for connection to the first medical device, and a body. The first connection member and the body are connected directly or indirectly together via at least one designated ruptureable retaining member, the at least one designated ruptureable retaining member is/are arranged to rupture when subjected to a predetermined breaking force. Wherein the first connection member and thereby the first medical device after assembly can be substantially displaced with respect to the body after rupture. The mentioned breaking force can be a shearing force, a compressive force, tensile force or combinations thereof.

The present invention provides for a substantially tamper resistant connection arrangement which can be used on substantially any medical device for a tamper resistant connection. The tamper resistant connection arrangement eliminates or at least reduces the risk of becoming disconnected from medical devices after it has been connected thereto. Thereby the risk of accidental leakage is significantly reduced and as a direct consequence of this, the environment and work safety for a user is improved as leakage of e.g. toxic drugs can be minimized. These advantages and others will be clear after reading the detailed description below.

In an embodiment according to the present invention, the first connection member is arranged to connect to the at least one first medical device by means of a threaded coupling in a first direction. As such a secure and simple coupling can be provided.

The at least one designated ruptureable retaining member can be arranged to rupture by means of a relative rotational motion subjected to the body with respect to the first connection member. Optionally a longitudinal motion along a centre axis could be used or combinations thereof. However, when using a relative rotational motion, the rupture of the designated ruptureable retaining members can be done by using the same rotational motion as used when connecting the first medical device to the connection arrangement. In this embodiment, the first direction is the same as the direction of the relative rotational motion.

Evaluation of the present invention has shown that the predetermined breaking force should preferably be between 10-40 Ncm, preferably 15-30 Ncm, the breaking force can be a shearing force. This ensures a high enough force, e.g. shear force, to enable a secure and tight connection while at the same time not use too much force to rupture the at least one designated ruptureable retaining member(s). As such the specific numbers of the designated ruptureable retaining members can be adapted so that a specific threshold break force can be obtained. For example 1-10 designated ruptureable retaining members can be used.

In an embodiment, according to the present invention, the at least one designated ruptureable retaining member is/are arranged to provide for a substantially planar fracture surface, to minimize the available friction forces between the body and the first connection member. After rupture it is important that the body and the first connection member can be displaced, for example by being enabled to freely rotate, with respect to each other as easily as possible. This reduces the risk of the first connection member and the body inadvertently engaging each other again, by a temporarily increased friction there between, or for any other reason. The fracture surface created after rupture is advantageously steered to an advantageous position, for example by the at least one designated ruptureable retaining member comprises at least one notch, an example of a suitable notch can be a groove in the designated ruptureable retaining member, a weak point, a fold or combinations thereof.

In yet an embodiment, according to the present invention, the first connection member and at least a part of the body together form a first connection site to which the first medical device can be connected. This is very advantageous when the connection arrangement is of luer-lock type, for example a female luer lock or a male luer lock connection. Usually in these cases, optionally in others, it is advantageous that the first connection member has a substantially cylindrical form. As such, the cylindrical form can at least partly enclose the body which then forms a part of the first connection site to enable a liquid tight seal there between.

The at least one designated ruptureable retaining member can be integrally formed with at least the first connection member and the body. Either way, the at least one designated ruptureable retaining member can be integrally formed with the members which after rupture are intended to be displaced, e.g., freely rotateable, with respect to each other. This enables the member to be manufactured in one piece, for instance by form moulding. Optionally, the at least one designated ruptureable retaining member is manufactured from a separate piece, which enables a large variety of the property of the at least one designated ruptureable retaining member, combinations thereof are of course also possible.

In an embodiment, according to the present invention, the body comprises means for substantially preventing the first connection member from motion along the centre axis A. These means can be a supportive housing, a circumferential groove which is intended to be assembled with a lock flange, for instance a wedge like protrusion, as is described in greater detail below.

In an embodiment according to the present invention, the first connection member comprises a first connection site to which the first medical device can be connected. In contrary to when the first connection member forms part of a first connection site together with the body, this embodiment may have a first connection site arranged on the first connection member. In this embodiment, the connection function to the first medical device and the first connection member are separated from each other, enabling a different use, for instance as is shown and described with reference to FIGS. 6-10 below.

The connection arrangement can comprise a second connection site for connecting to a second medical device. The second connection site can be a part of the body or separate therefrom, for example positioned on a part of a piercing member protection device to which the connection arrangement, according to the present invention, can be arranged. Hence it is well within the boundaries of the present invention that the connection arrangement forms part of a medical adaptor device, a piercing member protection device, a syringe, an infusion bag connection system, or any other medical device.

The present invention further relates to a method for attaching a first medical device to a connection arrangement, according to the present invention, to form a substantially tamper resistant connection therebetween. The connection arrangement comprises a first connection member and a body. The method comprises the steps of;
attaching the first medical device to the first connection member by means of a motion in a first direction;
rupturing at least one designated ruptureable retaining member arranged between the first connection member and the body, by means of subjecting the at least one designated ruptureable retaining member(s) with a breaking force, so that the first connection member and the body can be displaced, e.g. freely rotated, with respect to each other. The at least one designated ruptureable retaining member can optionally be ruptured by means of a rotational motion, preferably in the first direction. The method provides for a safe and accurate way of connecting a first medical device to a connection arrangement, for example used on a medical adaptor device, piercing member protection device or any other medical device. As such the present invention also relates to such devices.

The present invention also relates to a female and a male coupling device.

Such a coupling device has a centre axis and is arranged for connection with at least a first medical device. The coupling device comprises a first connection site comprising a cylinder member having threads for providing a threaded coupling with a first medical device by means of a rotational motion in a first direction. The cylinder member comprises an inner and an outer surface. The coupling devices further exhibit a fluid transfer channel for enabling a fluid connection, wherein the cylinder member is arranged to at least partly encompass the fluid transfer channel. The fluid transfer channel extends inside of a body. The cylinder member is directly or indirectly connected to the body via at least one designated ruptureable retaining member, wherein the at least one designated ruptureable retaining member is/are arranged to rupture when subjected to a predetermined breaking force whereafter the cylinder member can be displaced, for example to be freely rotated around the centre axis, and with respect to the body. Such a coupling device provides for a tamper resistant coupling device which can advantageously be used for e.g. transferring toxic fluids since there is no or limited risk of disconnection as e.g. the rotational motion needed for disconnection has been effectively disabled.

The female or male coupling device may comprise means for substantially preventing the cylinder from motion in a direction along the centre axis A, for example, the means may be a supportive housing arranged to hold the cylinder in position.

In an embodiment, the coupling device is a female coupling device and the threads of the cylinder member are arranged on the outer surface of the cylinder member. This is very useful on e.g. a syringe, such as a disposable syringe. Such a coupling device is arranged to receive a male coupling device outside on the cylinder member. In an embodiment, the female or male coupling device is a male coupling device and in that the threads of the cylinder member are arranged on the inner surface of the cylinder member. Such a coupling device is arranged to receive a female coupling device in the cylinder member.

In an embodiment according to the present invention, the at least one designated ruptureable retaining member is/are arranged to rupture when subjected to a rotational motion to the cylinder member and in that the imparted rotational motion is in the same direction as the first direction. This provides for the same advantages as mentioned above.

The designated ruptureable retaining members can be positioned in many different places. Generally the manufacturing methods determine the positioning. The cylinder member comprises a first and a second end and the at least one designated ruptureable retaining member is/are arranged at the first end of the cylinder member. This has been found to be advantageous from manufacturing point of view. The female or male coupling device as described above can be of a luer lock type connection.

The present invention also relates to a medical adaptor device, a piercing member protection device, a syringe, preferably a disposable syringe, an infusion bag connection system, or any other medical device having a connection arrangement as described above.

DEFINITIONS

By the term "medical device" as used in this document is meant any device which is suitable to use in a hospital environment, care taking environment, nursing institutions or the like, more preferably it is meant devices used in a hospital like environment requiring quality secured devices.

BRIEF DESCRIPTION OF THE DRAWINGS

The present invention will hereafter be described in greater detail and with reference to the accompanying figures in which;

FIG. 3b shows a cross section of the supportive housing as seen in FIGS. 1 and 3a;

DETAILED DESCRIPTION OF PREFERRED EMBODIMENTS

Figure 1:
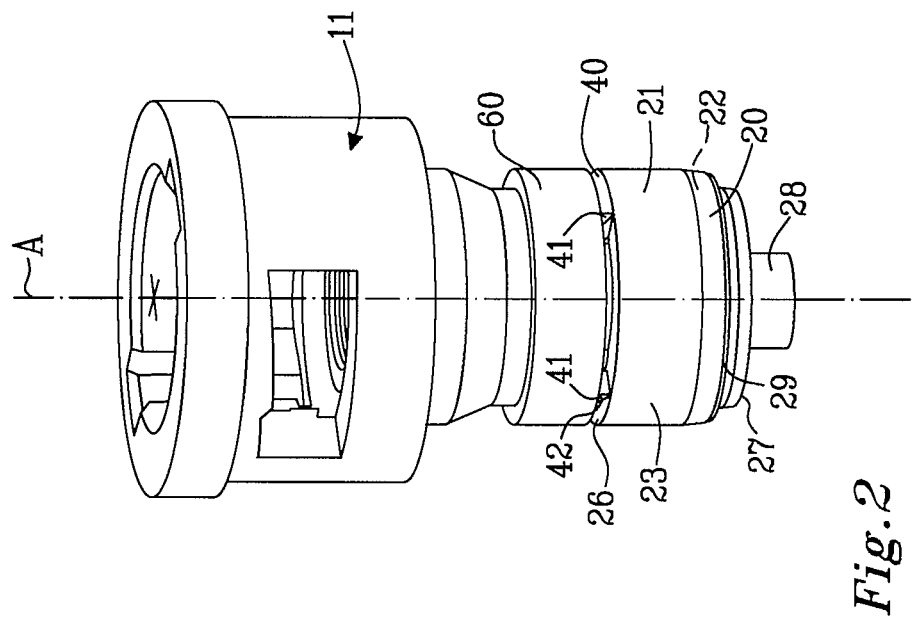
FIG. 1 shows a medical adaptor device having a connection arrangement according to an embodiment of the present invention.

The present invention will be described in greater detail and in a non limiting way with reference to the enclosed embodiments. FIG. 1 shows a connection arrangement 1 having a centre axis A, according to a first embodiment of the present invention, in the form of a medical adaptor device 10 for connecting to a syringe, a vial or any other medical device having a luer lock connection, and e.g. a medical device from the Carmel Pharma™ product range, using a double membrane coupling. A medical device using a double membrane coupling is described in the publication of WO 2008/115102A1.

The medical adaptor device 10 comprises a second connection site 11 for connecting with a medical device via a membrane coupling 12 having a neck element 13 and a first and a second guiding groove 14, 15 for guiding corresponding parts of a membrane coupling between a locked position and an unlocked position with a rotational motion. A barrier member 16 provides for a gas and liquid tight seal around a piercing member which during use is intended to be inserted into the barrier member 16 to e.g. administrate drugs. The medical adaptor 10 further comprises a first connection site 20 to connect to e.g. an injection port or a port an infusion bag, via a luer lock type connection 20. A supportive housing 30 is arranged to structurally support at least the second connection site 20.

Figure 2:
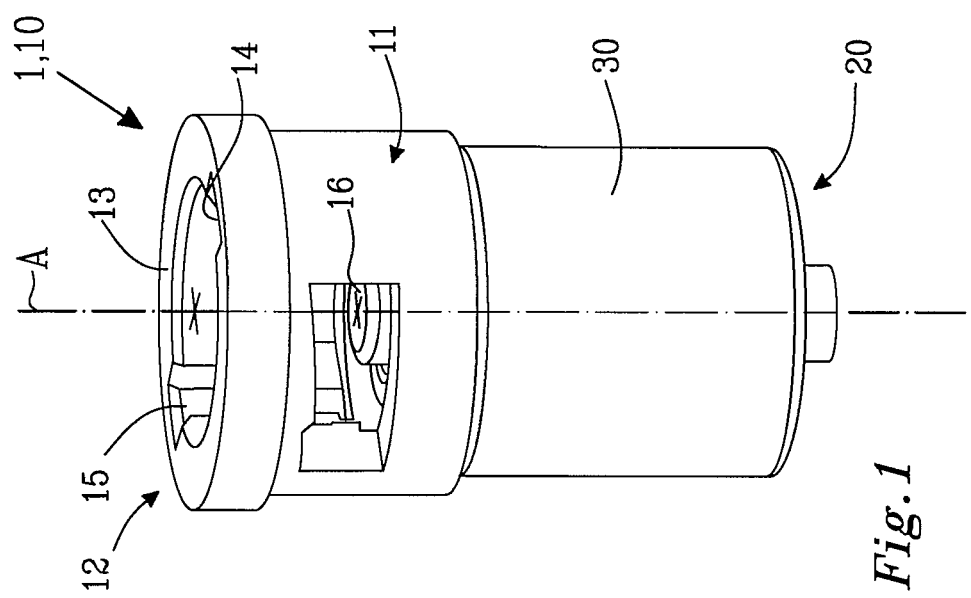
FIG. 2 shows parts of the medical adaptor device as seen in FIG. 1.
Figure 4:
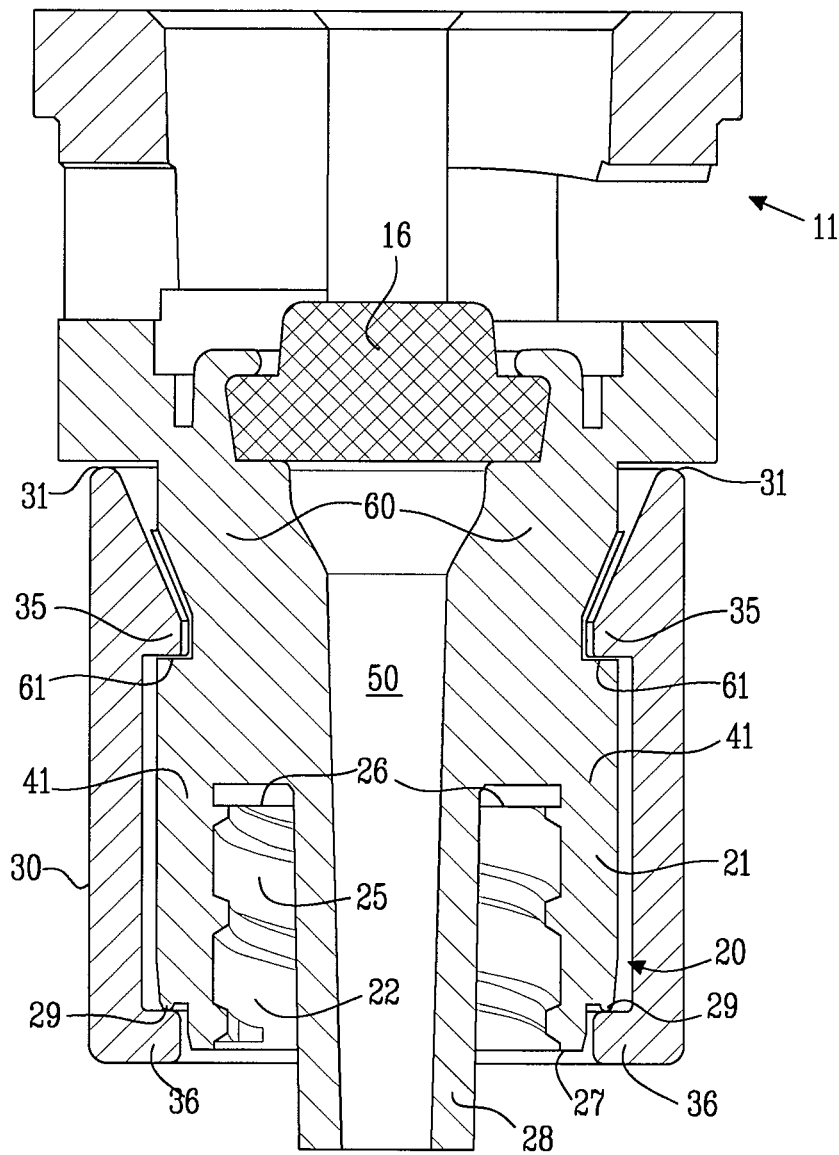
FIG. 4 shows a cross section of the medical adaptor device as shown in FIG. 1.

FIG. 2 shows the first and the second connection sites 20, 11 and a body 60, shown without the barrier member 16. The first connection site 20, i.e. the luer lock type connection, comprises a female cylinder 21 with an inner surface 22 and an outer surface 23, female in the sense that the female cylinder 21 is arranged to receive a male counterpart. The inner surface 22 of the female cylinder 21 exhibit threads 25 as shown in FIGS. 4-5. The female cylinder 21 has an upper and lower edge 26, 27. As can be seen a male tapered connection part 28 can be seen extending past the lower edge 27 of the female cylinder 21, as such, the first connection site 20 is generally referred to as a male luer-lock. At least partly defining the upper edge 26 of the female cylinder 21 of the first connection site 20 is a groove 40 extending around the periphery of the female cylinder 21 and extending through the width of the wall of the female cylinder 21. Four designated ruptureable retaining members 41 (only two of which are shown in FIG. 2) hold the female cylinder 21 is a fixed position with respect to the second connection site 11 and the body 60. The female cylinder 21 further; comprises, is arranged to, or is optionally in working cooperation with means for preventing the female cylinder 21 from motion along the centre axis A and especially in a direction away from the second connection site 11. In the shown embodiment, according to the present invention, the means comprises a stop flange 29 arranged in the proximity of the second end 27 of the female cylinder 21 and extending around the periphery of the female cylinder 21, and which is arranged in working cooperation with the supportive housing 30, as shown in FIG. 1.

FIG. 2 further show two of the four designated ruptureable retaining members 41 positioned symmetrically around the centre axis A at 90° intervals. Each of the four designated ruptureable retaining members 41 are adapted to rupture when subjected to a predetermined shear force subjected to the designated ruptureable retaining members 41 preferably after the assembly with a first medical device, and preferably with a substantially planar fracture surface so that the friction forces between the body 60 and the female cylinder 21 is kept as low as possible to prevent the first medical device being unscrewed.

The form and shape of the designated ruptureable retaining members 41, and for the sake of the present invention, any at least one designated ruptureable retaining member(s), is preferably adapted to provide a fracture surface which minimizes the friction between the rotating parts, in the shown embodiment of FIG. 2, between the female cylinder 21 and the body 60. This can preferably be done by providing the designated ruptureable retaining members with a notch to steer the location of the fracture surface. This is also preferable for all the embodiments described hereafter. In the embodiment, according to the present invention, shown in FIG. 2, the designated ruptureable retaining members 41 are formed having a tilting surface 42, tilting towards the first end 26 of the female cylinder 21. In this case, the notch is tangential to the first end 26 of the female cylinder 21, providing a fracture surface at the first end 26 of the female cylinder 21. Furthermore, the manufacturing material is preferably chosen so that the fracture surface is substantially parallel with the first end 26 of the female cylinder 21 to minimize the friction there between. The tilting surface 42 is preferably arranged so that it provides for a slope towards the unscrewing direction to reduce the friction formed between the female cylinder 21 and the body 60. This is of course applicable to all embodiments herein.

Figure 3B:
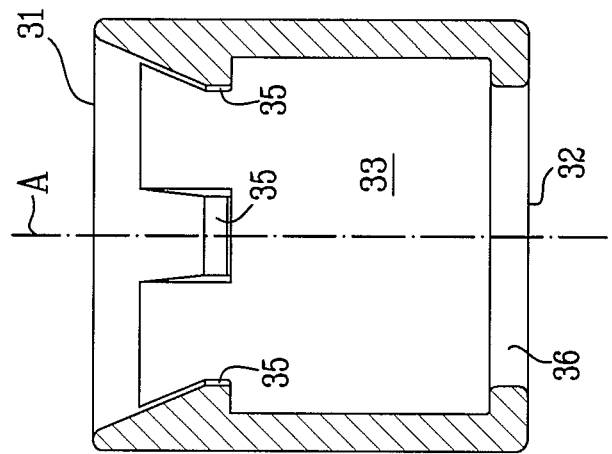
Figure 3A:
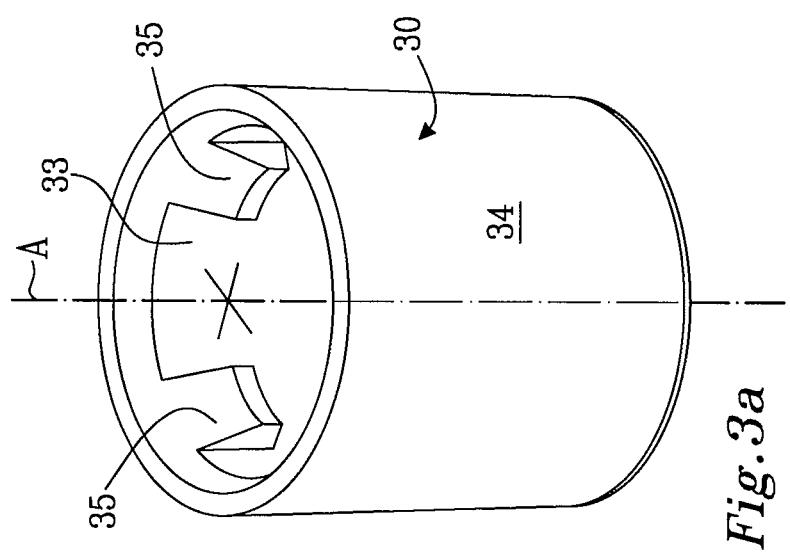
FIG. 3a shows the supportive housing of the medical adaptor as seen in FIG. 1.

FIGS. 3a-3b show the supportive housing 30 in greater detail and separated from the other parts of the medical adaptor device 10 for the sake of clarity. The supportive housing 30 has a substantially cylindrical form having an upper and a lower end, equivalent to a first and a second end 31, 32 and an inner and an outer surface 33, 34. A plurality of, in this embodiment four, wedge like protrusions 35 extend out from the inner surface 33 of the supportive housing 30 in the proximity of the first end 31, although only two wedge like protrusions 35 are shown in FIGS. 3a-3b. The wedge like protrusions 35 have a tapering surface, tapering towards the first end 31 of the supportive housing 30. At the second end 32 of the supportive housing 30 is a circumferential stop flange 36, which extends around the inner surface 33 and protrudes towards the centre axis A. The purpose of the circumferential stop flange 36 and the wedge like protrusions 35 will be described in greater detail below.

FIG. 4 shows a cross section of the medical adaptor device 10 shown in FIG. 1. More specifically, FIG. 4 shows the second connection site 11 with the barrier member 16, the first connection site 20 and a fluid channel 50 extending there between. A body 60 defines the fluid channel 50 and the male tapered connection part 28 as can be seen extending past the lower edge 27 of the female cylinder 21. The supportive housing 30 encloses the female cylinder 21 of the first connection site 20. During assembly, the supportive housing 30 is slid onto the female cylinder 21 until the wedge like protrusions 35 snap onto a lock flange 61, which extends around the periphery of the body 60. The wedge like protrusions 35 and the lock flange 61 of the body 60 prevent the supporting housing 30 from movement along the centre axis A. In addition, the second connection site 11 can be arranged to be positioned adjacent the upper end 31 of the supportive housing 30 to prevent the supportive housing from movement along the centre axis A, at least in one direction. As can further be seen in FIG. 4, the circumferential stop flange 36 of the supportive housing 30 is, after assembly, positioned substantially adjacent the corresponding stop flange 29 of the female cylinder 21. Optionally part of the second end 27 of the female cylinder 21 can be used to cooperate with the circumferential stop flange 36.

The supportive housing 30 permits the female cylinder to rotate around the centre axis A, after the designated ruptureable retaining members 41 are ruptured. It further keeps the female cylinder 21 from motion in the longitudinal direction of the centre axis A. This enables the medical adaptor device 10 to be tamper resistant in the meaning of that any device which is attached with the medical adaptor device 10 can, after the at least one designated ruptureable retaining member is/are ruptured, freely rotate. In practice, the effect of this is that the second connection site 11 uses a rotational motion to fasten a medical device, for the sake of this example; an injector. The same rotational motion can be used to rupture the designated ruptureable retaining members 41 whereafter the friction between the female cylinder 21 and the body 60 and the supportive housing 30 is so low that a counter rotational motion does not unscrew the injector. This function and effect will be described in greater detail with reference to FIGS. 5a-5b.

Figure 5A:
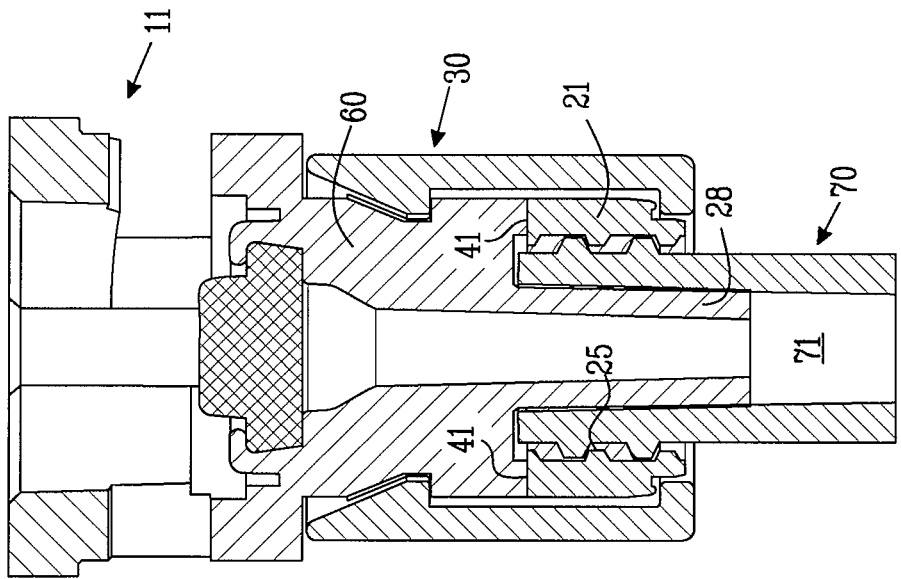
FIG. 5a shows a cross section of the medical adaptor device as shown in FIG. 1 after connection with a female catheter connection part.
Figure 5B:
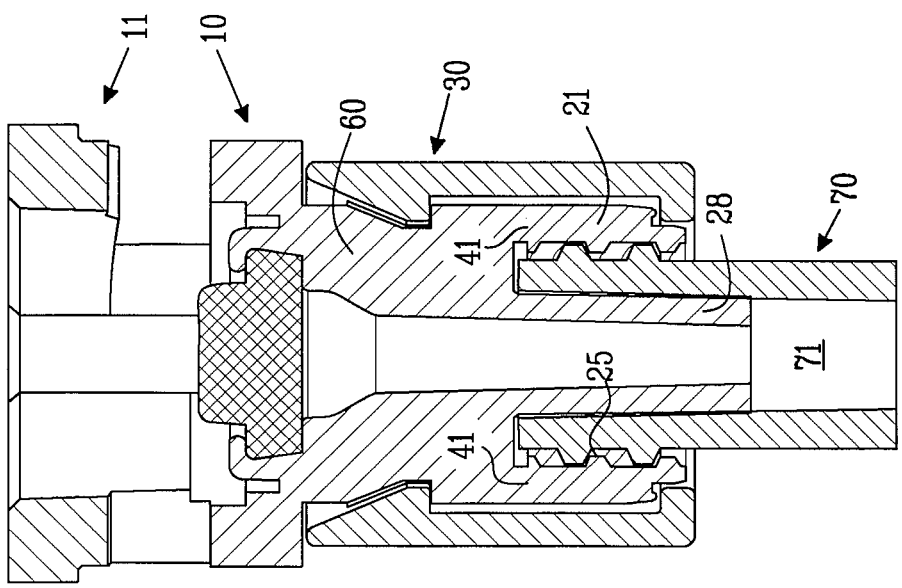
FIG. 5b shows a cross section of the medical adaptor device as shown in FIG. 5a after connection with a female catheter connection part and after rupture of the designated ruptureable retaining members.

FIGS. 5a-5b show the medical adaptor device 10 as shown in FIG. 1 and FIG. 4 after connection with a female catheter connection part 70. The female catheter connection part 70 has been screwed onto the threads 25 of the female cylinder 21 until the male tapered connection part 28 of the body 60 engages the inner surface 71 of the female catheter connection part 70. When continuing the rotational motion, i.e. the threading, the friction between the male tapered connection part 28 and the inner surface 71 of the female catheter connection part 70 is sufficiently high to provide for a good connection and a substantially liquid tight seal therebetween. As the rotational motion is continued, the designated ruptureable retaining members 41 rupture. As can be seen in FIG. 5a, the designated ruptureable retaining members 41 are formed integrally with the body 60 and the female cylinder 21 of the medical adaptor device 10, for example by form molding with a thermoplastic material. In other embodiments, according to the present invention, the at least one designated ruptureable retaining member(s) 41 can be made form different material(s), combinations of integrally formed designated ruptureable retaining members 41 and designated ruptureable retaining members 41 made from different materials are of course also possible, each embodiment having its own advantage. For instance, if the medical connector device is manufactured from a metal material it might be advantageous to have the designated ruptureable retaining members 41 manufactured in a thermoplastic material.

Further, the at least one designated ruptureable retaining member(s) can be manufactured from a substantially elastic material. This could be advantageous since a user could be warned or informed of when the designated ruptureable retaining members 41 are about to break by an indication on the connector, in this case the medical adaptor device 10, corresponding to the required rotational distance before rupture, which can be calculated or evaluated.

FIG. 5b shows the female catheter connection part 70 after being connected to the luer lock type connection of the medical adaptor device 10. The female catheter connection part 70 can now be connected to a medical device having a double membrane bayonet coupling via the medical adaptor device 10. As can further be seen, the designated ruptureable retaining members 41 have ruptured, thereby permitting the female cylinder 21 to be freely rotated around the centre axis A, while being substantially prevented from motion in a longitudinal direction of the centre axis A, i.e. in a motion along the centre axis A. As the female cylinder 21 can be freely rotated, the second connection site 11 can also be freely rotated, with respect to the first connection site 20, i.e. the luer lock connection and the female catheter connection part 70. Hence, the medical adaptor device 10 in principle cannot be removed from the female catheter connection part 70.

It is further notable that the risk of leakage between the inner surface 71 of the female catheter connection part 70 and the male tapered connection part 28 is very low. In fact, the male tapered connection part 28 can be rotated inside of the female catheter connection part 70 without leakage. Should it be desirable for any reason to further improve the leakage preventive properties of the medical adaptor device 10, the medical adaptor device 10 can be provided with at least one leakage barrier, preferably in the near proximity of the root of the male tapered connection part 28, such as an O-ring, which after assembly is intended to be positioned adjacent the attached medical device, in the shown embodiment, the top of the female catheter connection part 70. The connection arrangement 1, in this case the medical adaptor device 10, can be coated with a leakage preventing coating such as a silicone based coating. In this case the coating would be applied onto the male tapered connection part 28.

It is further notable that the supportive housing 30 can be arranged with means to prevent it from rotation with respect to the second connection site 11. Such means may be in the form of a protrusion and a corresponding groove. This feature would improve the handling of the medical adaptor device 10 by providing a larger grip area.

Injector

The present invention will be further described with reference to a second embodiment according to the present invention. In this embodiment, the connection arrangement 1 is applied to a piercing member protection device 99 for providing at least a first medical device with a substantially tamper resistant connection. Suitable piercing member protection device which can be utilized is disclosed in the patent application publication of WO2008/115102 in the name of Carmel Pharma AB.

Figure 6:
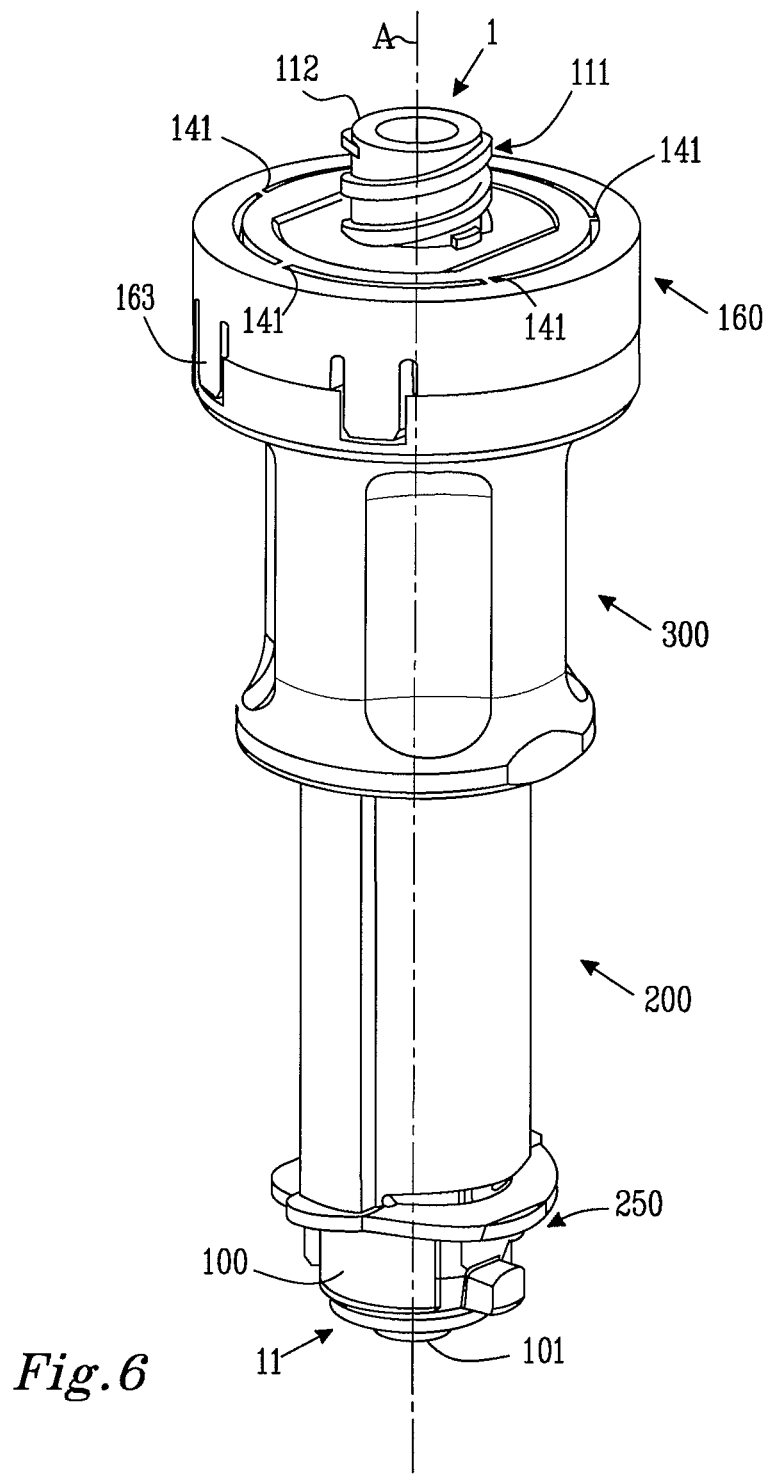
FIG. 6 shows a piercing member protection device having a connection arrangement according to an embodiment of the present invention.

FIG. 6 shows the piercing member protection device 99 with a longitudinal centre axis A extending in the longitudinal direction of the piercing member protection device 99 and in the centre of the piercing member protection device 99. Generally the piercing member protection device 99 exhibits a first cylindrical member 100 which is at least partly encompassed by a second cylindrical member 200, which in turn is at least partly encompassed by a third cylindrical member 300. A piercing member (not shown) is connected to the third cylindrical member 300 and extends into a protection chamber defined by the interior of the first cylindrical member 100. A first barrier member 101, which after connection with a connection port on e.g. an infusion bag is intended to provide a double membrane coupling, seals the protection chamber of the first cylindrical member 100 to provide a closed environment for at least the tip of the piercing member of the piercing member protection device 99. This position is also referred to as the unexposed state, as the piercing member is unexposed inside the protective chamber.

A first locking arrangement 250 is provided between the first cylindrical member 100 and the second cylindrical member 200. The first locking arrangement 250 can be arranged in a first position in which the first cylindrical member 100 is enabled to be turned with respect to the second cylindrical member 200 and a second position in which the first cylindrical member 100 is disabled form turning with respect to the second cylindrical member 200. The second locking device can be alternated between the first and the second position by means of connecting the piercing member protection device 99 to the connection port.

A second locking arrangement provides a first position in which the piercing member, and the third cylindrical member 300, is enabled to move along the centre axis A with respect to the first barrier member 101, and a second position in which the piercing member, and the third cylindrical member 300, is prevented from moving along the longitudinal centre axis A with respect to the first barrier member 101. The second locking arrangement 350 is alternated between the first position and the second position by means of turning the first cylindrical member 100 and the third cylindrical member 300 with respect to the second cylindrical member 200. As the piercing member is moved along the longitudinal centre axis A it can be moved to an exposed state at which parts of the piercing member are exposed outside of the protective chamber and the first barrier member 101, for example in order to transfer a drug from a vial to a syringe. The second locking arrangement is enabled by an L-shaped groove on the third cylindrical member 300 and a corresponding protrusion on the second cylindrical member 200.

As can further be seen in FIG. 6, the third cylindrical member 300 comprises a first connection site 111 having a threaded female connection part 112 for connection with a male luer lock connection on e.g. a syringe. The first connection site 111 is connected to the third cylinder member 300 via at least one ruptureable retaining member 141, in the shown embodiment of FIG. 6, five designated ruptureable retaining members 141, although only four can be seen. This permits the first connection site 111 to freely rotate around the centre axis A, after the designated ruptureable retaining members 141 are ruptured. It further prevents the first connection site 111 from motion in the longitudinal direction of the centre axis A. This enables the piercing member protection device 99 to be tamper resistant in the meaning of that any device which is attached to the piercing member protection device 99 can, after the at least one designated ruptureable retaining member is/are ruptured, freely rotate. In practice, the effect of this is that since the first connection site 111 uses a rotational motion to fasten a medical device, for the sake of this example; a syringe. The same rotational motion can be used to rupture the designated ruptureable retaining members 141 whereafter the friction between the first connection site 111 and the third cylinder member 300 is so low that a counter rotational motion does not unscrew the medical device, in this case a syringe.

Figure 7:
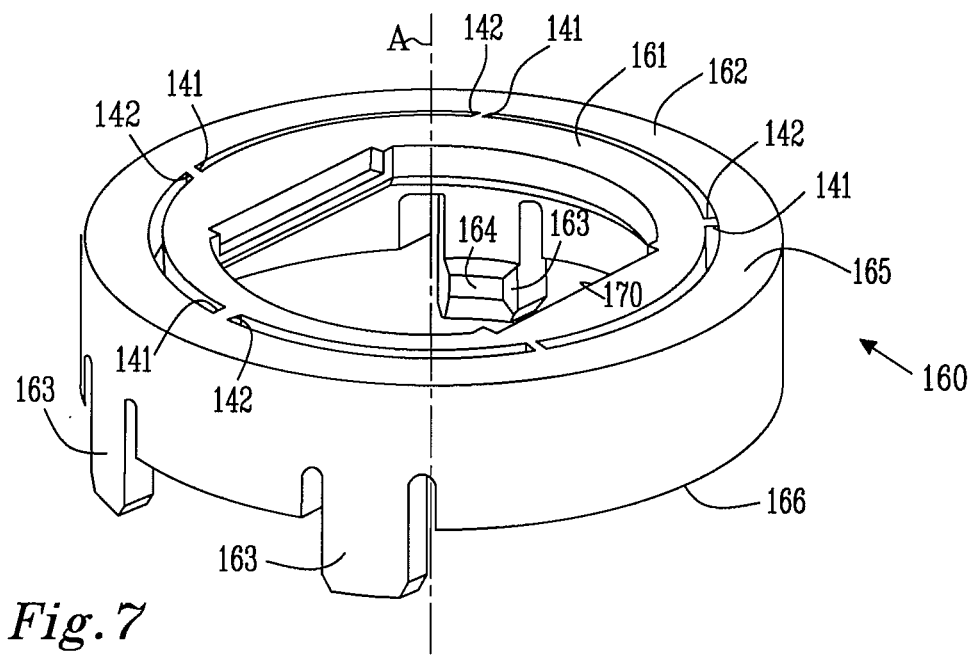
FIG. 7-9 shows the parts of the piercing member protection device as seen on FIG. 6 in greater detail.

In the embodiment shown in FIG. 6, the designated ruptureable retaining members 141 are assembled to the piercing member protection device 99 via a ring body 160 having an inner and an outer ring member 161, 162, as seen in greater detail in FIG. 7. By the terms inner and outer rings, is meant with reference to the centre axis A. FIG. 7 shows further that the outer ring member 161 comprises a plurality of deformable lock flanges 163 which are arranged to, during assembly, deform so that the deformable lock flanges 163 can be positioned to engage and lock the ring body 160 to the third cylinder member 300 at a plurality of corresponding lock grooves 310 (shown in FIG. 9). Each deformable lock flange 163 comprises a lock protrusion extending from the distal end of the deformable lock flanges 163 towards the centre axis A.

The ring body 160 also exhibits a first and a second end 165, 166, equivalent to the upper and the lower end 165, 166 as seen in FIG. 7. In the near proximity of the first end 165 of the ring body 160, five designated ruptureable retaining members 141 attach the inner ring member 161 to the outer ring member 162 preventing the inner ring member 161 from substantially any motion with respect to the outer ring member 162 before the designated ruptureable retaining members 141 are ruptured by a predetermined shear force. Each of the designated ruptureable retaining members 141 exhibit a tilting surface 142 serving the purpose of reducing the friction forces and minimizing the risk for reengagement of the fractured parts, between the inner and outer ring member 161, 162 after the designated ruptureable retaining members 141 have been ruptured. The designated ruptureable retaining members 141 are made integrally with the cylindrical body 160. However, as mentioned earlier, they can be made from different materials or combinations thereof.

Figure 8:
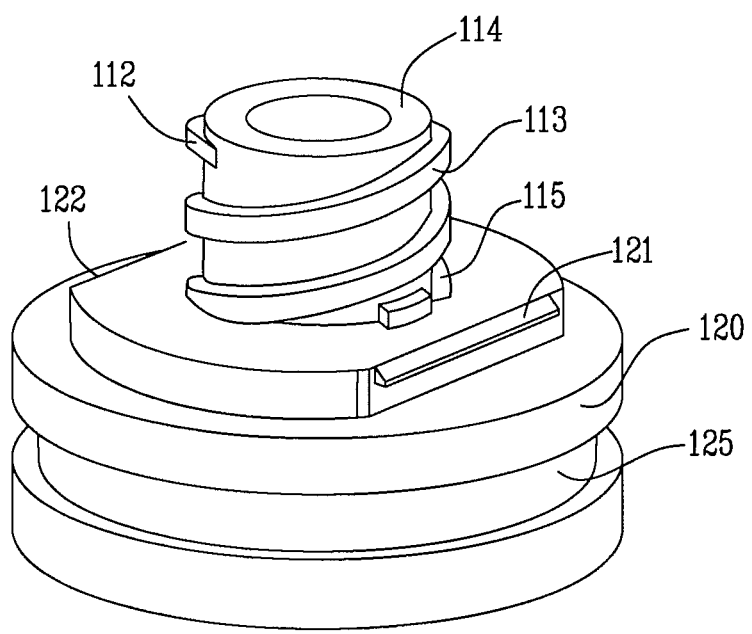

The inner ring 161 comprises attachment flanges 170 to provide a snap on connection between the first connection site 111 and the inner ring 161. FIG. 8 shows the first connection site 111 in greater detail. As can be seen, the first connection site 111 comprises a threaded female connection part 112 equipped with threads 113 for a rotational connection with a medical device (not shown) such as a syringe. The threaded female connection part 112 comprises a distal end 114 and a proximal end 115. The proximal end 115 of the threaded female connection part 112 is arranged on a cylindrical base 120 having a first and a second locking flange 121, 122 for providing a snap on connection with the inner ring 161 and the corresponding attachment flanges 170. Furthermore, the cylindrical base 120 comprises a circumferential channel 125 extend around the periphery of the cylindrical base 120 permitting, after assembly, free rotation of the cylindrical base 120 with respect to the third cylinder 300 of the piercing member protection device 99.

As is noticed, the cylindrical base 120 and the inner ring member 161 of the ring body 160 forms the body while the outer ring 162 and optionally the third cylinder member 300 forms a first connection member.

Figure 9:
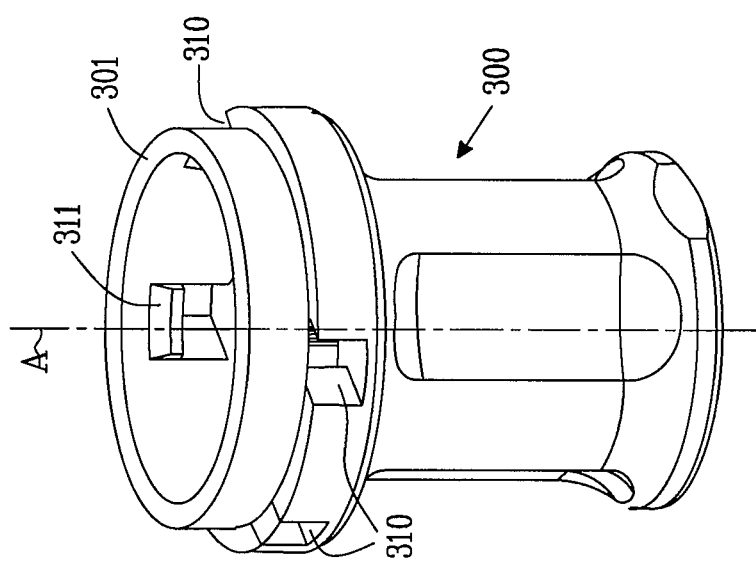

FIG. 9 shows the third cylinder member 300 in greater detail without any other components attached. As can be seen, the third cylinder member 300 comprises a plurality of lock grooves 310 for connection with the ring body 160 and the deformable lock flanges 163 of the outer ring 162 of the ring body 160. Wedge like protrusions 311 are arranged on the inside of the third cylinder member 300 in the proximity of an upper end 301 of the third cylinder member 300, and extending towards the centre axis A enabling a snap on connection with the circumferential channel 125 of the cylinder base 120.

Figure 10:
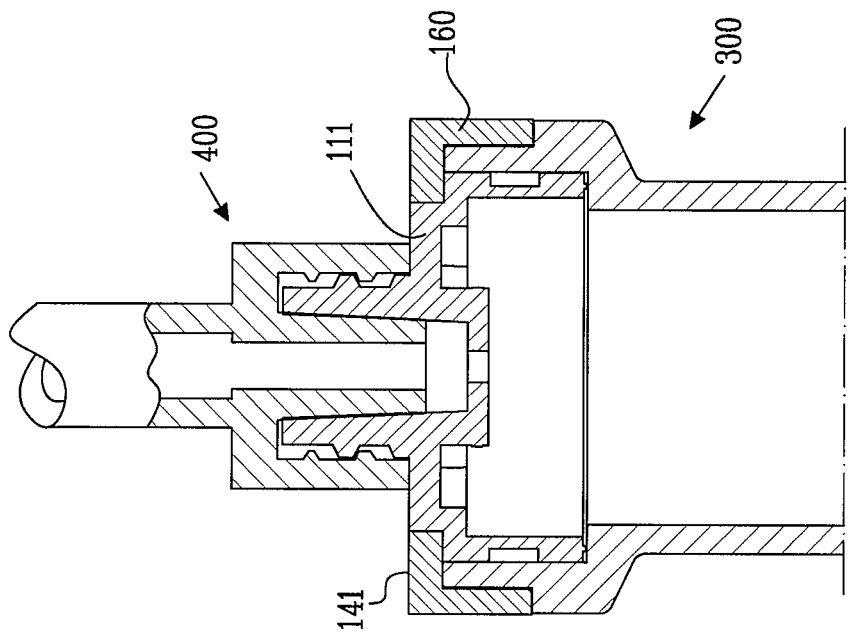
FIG. 10 shows parts of the piercing member protection device after assembly with a tube.

FIG. 10 shows a cross section of the third cylinder member 300, the ring body 160 and the first connection site 11 after assembly and before rupture of the designated ruptureable retaining members 141. An infusion tube 400 is threaded onto the threaded female connection part 112 of the first connection site 111. As the infusion tube 400 is connected by a rotational motion, the luer lock connection provides for a liquid tight seal between the first connection site 111 and the infusion tube 400. As the rotational motion continues, the connection is tightened and a predetermined threshold of stress, in this case about 25 Ncm, the shear force imparted from the infusion tube 400 ruptures the designated ruptureable retaining members 141 of the cylindrical body 160. As the designated ruptureable retaining members 141 of the cylindrical body 160 rupture, the inner ring 161 of the cylindrical body 160 is permitted to freely rotate around the centre axis A, disabling any attempts to disconnect the infusion tube 400.

Infusion Bag

Figure 11:
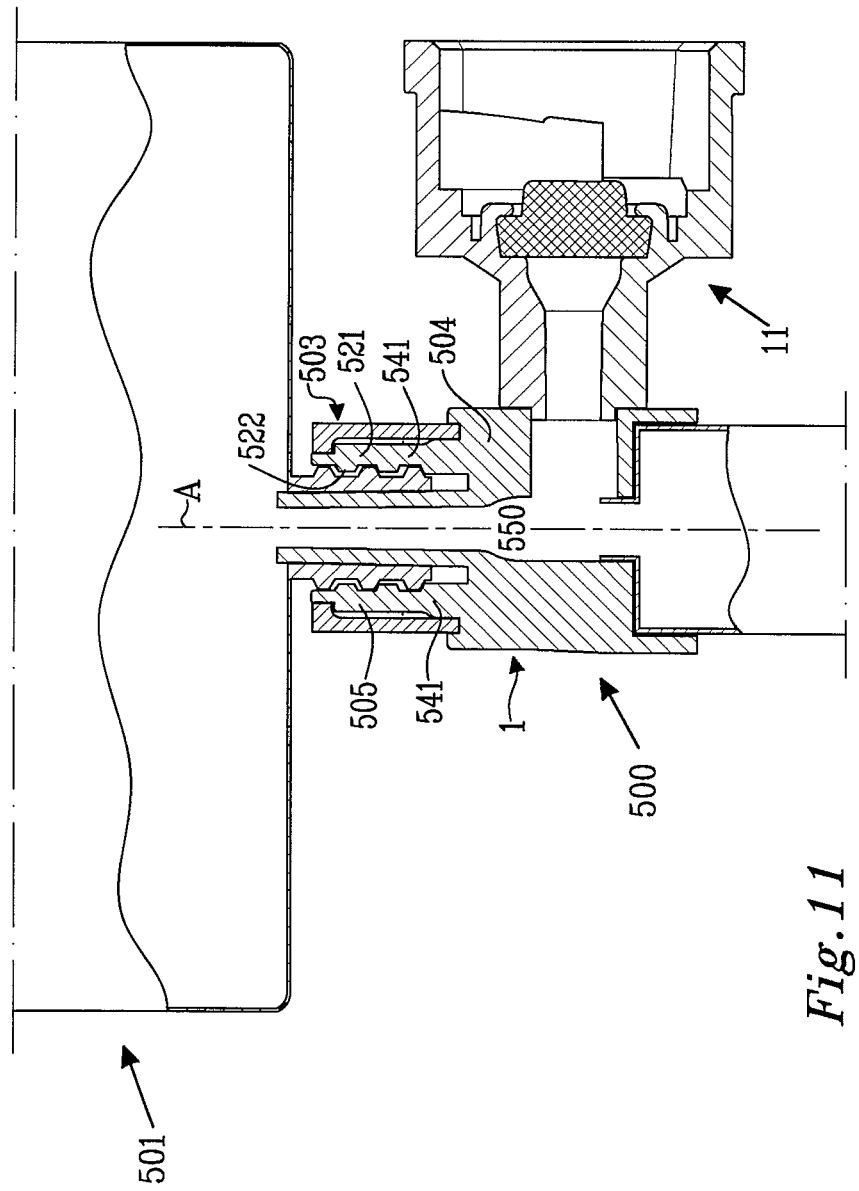
FIG. 11 shows parts of an infusion bag connection system having a connection arrangement according to an embodiment of the present invention.

In a third embodiment according to the present invention, the connection arrangement is utilized on an infusion bag connection system 500 for a tamper resistant connection to an infusion bag 501. As is seen in FIG. 11, the infusion bag connection system 500 comprises a second connection site 503, as described earlier with reference to FIGS. 4 and 5a-5b. That is, a body, a first connection member 505, in the form of a female cylinder 521 having a threaded inner surface 522, is fixedly connected to the body 504 by means of at least one designated ruptureable retaining member, which after subjected to a predetermined shear force is arranged to rupture. After rupture the female cylinder 521 can be freely rotated around the centre axis A with respect to the body 504. A fluid transfer channel 550 is arranged in the body 504.

As has been shown, the connection arrangement 1 according to present invention can advantageously be used as a male luer lock connection. Additionally the connection arrangement 1 can be used on, i.e. as the connection arrangement on a medical device e.g. a syringe, such as a disposable syringe, a medical fluid container, a medical waste container or the like.

Female Luer Lock Type Connection

Figure 12A:
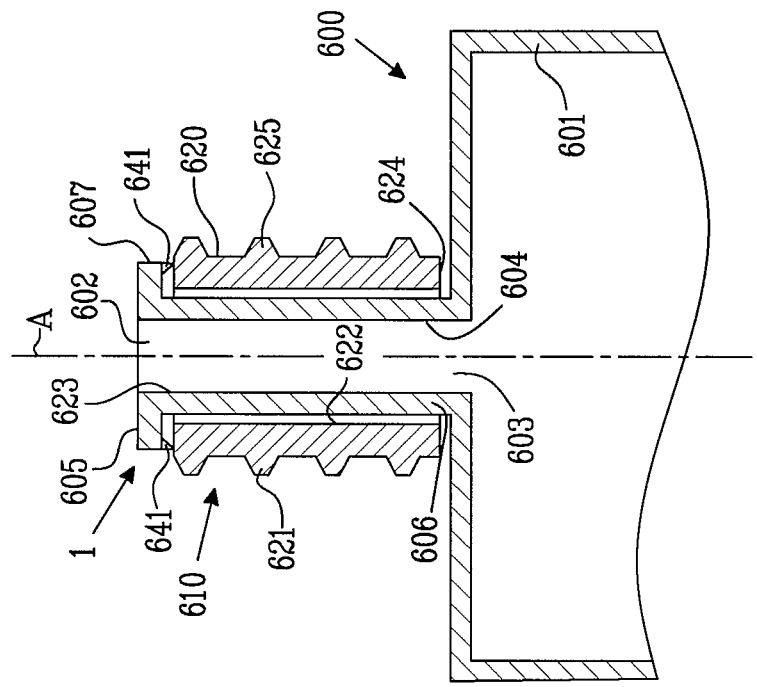
FIG. 12a-12b shows a disposable syringe having a connection arrangement according to an embodiment of the present invention.
Figure 12B:
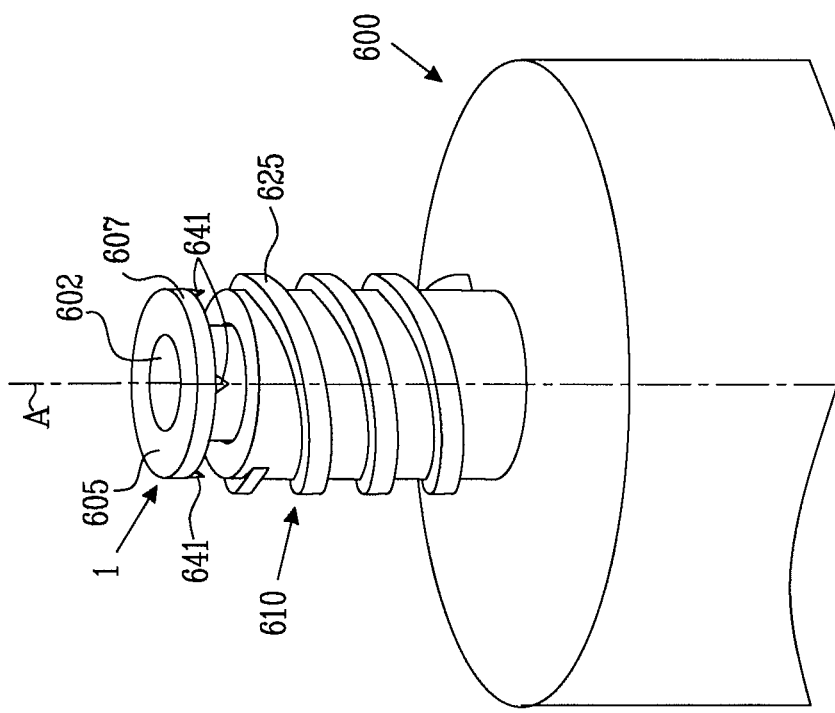

It is also within the boundaries of the present invention that the connection arrangement 1 is used as a female luer lock connection, as is shown in FIG. 12a-12b exemplified with a disposable syringe (only a part of the syringe is shown for the sake of clarity and without its plunger). FIG. 12a shows a cross section of a syringe 600 with a centre axis A and adapted for a tamper resistant connection with a first medical device, such as a piercing member protection device. FIG. 12b shows the syringe as seen in perspective. The syringe 600 is preferably of the disposable type.

With reference to both FIGS. 12a and 12b, the syringe 600 comprises a fluid housing 601 in which drugs can be temporarily contained before administration trough a dispensing opening 602, arranged in the end of the fluid housing 601. The fluid housing 601 further comprises a second opening (not shown) through which a plunger can be inserted for volumetric control of the fluid housing. The dispensing opening 602 comprises a dispensing channel housing 603 with a dispensing channel and with a slightly tapered inner surface 604, so as to be able to tightly mate with the male tapered connection part of a male luer lock connection, see for example the male tapered connection part 28 in FIG. 2 or FIG. 4. The dispensing channel housing 603 exhibit a distal end 605, and a proximal end 606 wherein the proximal end is arranged on the fluid housing 601 of the syringe 600.

A cylinder 620 having an outer and an inner surface 621, 622 and a first and a second end 623, 624 is arranged on the dispensing channel housing 603. The outer surface 621 facing away from the centre axis A. Threads 625 are arranged on the outer surface 621 of the cylinder 620 for connection with a male luer lock connection. The distal end 605 of the dispensing channel housing 603 comprises a circumferential lock flange 607 to substantially prevent the cylinder 620 from motion in a direction along the centre axis A, at least in a direction away from the fluid housing 601, the fluid housing 601 being a natural stop in the other direction.

As is noted, the dispensing channel housing 603 form together with the fluid housing 601 a body while the cylinder 620 form a first connection member. A connection site 610 is formed by the dispensing channel housing 603 and the cylinder 620.

The cylinder 620 is attached to the circumferential lock flange 607 via a plurality of designated ruptureable retaining members 641. The designated ruptureable retaining members 641 prevent the rotation of the cylinder 620 with respect to the fluid housing 601 and thereby enabling the connection to a male luer lock connection. As the syringe is screwed on to the medical device and a tight connection is reached, the threshold shear force of each of the designated ruptureable retaining members 641 is surpassed, fracturing the ruputureable retaining members 641. As the designated ruptureable retaining members rupture, the cylinder 620 of the syringe 600 can rotate freely, with respect to the fluid housing 601 of the syringe, without risking that the syringe and the medical device is disconnected.

The fluid housing 601, the designated ruptureable retaining members 641, the cylinder 620, the circumferential lock flange 607 and the dispensing channel housing 603 can be formed integrally from the same material. Optionally, the designated ruptureable retaining members can be formed from another material; the cylinder 620 can be e.g. adhered to the dispensing channel housing 603 to form the designated ruptureable retaining members.

In the embodiments described above the rupture of the designated ruptureable retaining members is accomplished by a rotational motion in the same rotational direction as the connection of the first medical device. One major advantage of using this configuration of the connection arrangement, according to the present invention, is of course that it disables any attempt to counter-rotate the medical device after the designated ruptureable retaining members are ruptured. However, it is well within the boundaries of the present invention that the rupture of the designated ruptureable retaining member(s) can be done by means of pressing, pulling, tilting or otherwise manipulating e.g. the connected first medical device. The triggering mechanism for rupturing the designated ruptureable retaining member(s) are in some embodiments less relevant, although the rotational triggering is preferable since it can be combined with a rotational attachment of a medical device. Furthermore, the connection of the first medical device does not have to be by a rotational motion, instead is it possible to use e.g. a snap on connection.

Preferable material for manufacturing a connection arrangement according to the present invention as described above is polypropylene, polyethylene, PVC, polyurethane, acrylonitrile butadiene styrene (ABS), polystyrene, polyoxymethylene, polyethylene terephthalate, similar plastics or mixtures thereof, although other materials such as metal e.g. aluminum, steel, iron, brass, or alloys thereof are possible. Combinations of these materials are of course also possible.

The invention claimed is:

1. A connection arrangement for providing at least a first medical device with a substantially tamper resistant connection, said connection arrangement comprising;
   a first connection member for connection to said at least one first medical device;
   a second connection member having a membrane coupling having at least one guiding groove;
   a body having a lock flange extending around the periphery of the body;
   a supportive housing having a wedge protrusion;
   wherein said first connection member and said body are connected via at least one designated ruptureable retaining member that is integrally formed with the body and a cylinder of the first connection member and is arranged to rupture when subjected to a predetermined breaking force, and
   wherein said first connection member, and thereby said first medical device after assembly, can be displaced with respect to said body after rupture.

2. The connection arrangement according to claim 1, wherein said first connection member is arranged to connect to said first medical device by means of a threaded coupling in a first direction.

3. The connection arrangement according to claim 1, wherein said at least one designated ruptureable retaining member is arranged to rupture by means of a relative rotational motion imparted to said body with respect to said first connection member.

4. The connection arrangement according to claim 3, wherein said first direction is the same direction as said relative rotational motion.

5. The connection arrangement according to claim 4, wherein said first connection member and at least a part of said body together form a connection site to which said first medical device can be connected.

6. The connection arrangement according to claim 4, wherein said body comprises means for substantially preventing said first connection member from motion along a centre axis (A).

7. The connection arrangement according to claim 4, wherein said first connection member has a substantially partly cylindrical form.

8. The connection arrangement according to claim 7, wherein said first connection member comprises threads for a threaded coupling with said first medical device.

9. The connection arrangement according to claim 1, wherein said predetermined breaking force is between 10-40 Ncm.

10. The connection arrangement according to claim 9, wherein said predetermined breaking force is between 15-30 Ncm.

11. The connection arrangement according to claim 1, wherein at least one designated ruptureable retaining member is 1-10 designated ruptureable retaining members.

12. The connection arrangement according to claim 1, wherein at least one designated ruptureable retaining member is arranged to provide for a substantially planar fracture surface, to minimize the available friction forces between said body and said first connection member.

13. The connection arrangement according to claim 1, wherein at least one designated ruptureable retaining member comprises at least one notch to steer the position of a fracture surface.

14. The connection arrangement according to claim 1, wherein said first connection member comprises a connection site to which said first medical device can be connected.

15. The connection arrangement according to claim 1, wherein said body comprises a second connection site for connecting to a second medical device.

16. The connection arrangement according to claim 1, wherein said connection arrangement forms part of a medical adaptor device.

17. The connection arrangement according to claim 1, wherein said connection arrangement forms part of a piercing member protection device.

18. The connection arrangement according to claim 1, wherein said connection arrangement forms part of a syringe.

19. The connection arrangement according to claim 1, wherein said connection arrangement forms part of an infusion bag connection system.

20. A method for attaching a first medical device to a connection arrangement to form a substantially tamper resistant connection there between, said method comprising the steps of;
   attaching said first medical device to a first connection member of said connection arrangement by moving in a first direction;
   rupturing at least one designated ruptureable retaining member which is integrally formed with the first connection member and a body of said connection arrangement in a fixed position, by subjecting said designated ruptureable retaining member to a predetermined breaking force, so that a supportive housing permits said first connection member and said body to be displaced around a centre axis with respect to each other.

21. The method according to claim 20, wherein said at least one designated ruptureable retaining member is ruptured by means of a rotational motion in a first direction.

22. A female or a male coupling device having a centre axis A for connection with at least a first medical device, said coupling device comprising a connection site comprising;
   a cylinder member having threads for providing a threaded coupling with a first medical device by means of a rotational motion in a first direction, said cylinder member comprising an inner and an outer surface,
   a fluid transfer channel for enabling a fluid connection, wherein said cylinder member is arranged to at least partly encompass said fluid transfer channel, and
   a body having a lock flange extending around the periphery of the body, and
   a supportive housing having a wedge protrusion, said fluid transfer channel extending inside of said body, wherein said cylinder member is connected to said body via at least one designated ruptureable retaining member integrally formed with the body and the cylinder, wherein said at least one designated ruptureable retaining member is arranged to rupture at a predetermined breaking force whereafter said supportive housing permits said cylinder member to freely rotate around said centre axis (A) and with respect to said body.

23. The female or male coupling device according to claim 22, wherein said first connection site comprises means for substantially preventing said cylinder member from motion in a direction along said centre axis A.

24. The female or male coupling device according to claim 22, wherein said coupling device is a female coupling device and in that said threads of said cylinder member is arranged on said outer surface of said cylinder member.

25. The female or male coupling device according to claim 22, wherein said coupling device is a male coupling device and in that said threads of said cylinder member is arranged on said inner surface of said cylinder member.

26. The female or male coupling device according to claim 22, wherein said at least one designated ruptureable retaining member is arranged to rupture by a subjected rotational motion to said cylinder member and in that said subjected rotational motion is in the same direction as said first direction.

27. The female or male coupling device according to claim 22, wherein said cylinder member comprises a first and a second end and in that said at least one designated ruptureable retaining member is arranged to said first end of said cylinder member.

28. The female or male coupling device according to claim 22, wherein said coupling device is of a luer-lock connection type.

* * * * *